United States Patent [19]

Groch et al.

[11] 4,240,440
[45] Dec. 23, 1980

[54] METHOD AND APPARATUS FOR NUCLEAR KYMOGRAPHY PROVIDING A MOTION VERSUS TIME DISPLAY OF THE OUTER TRANSVERSE DIMENSIONS OF AN ORGAN

[75] Inventors: Mark W. Groch, Elk Grove Village; George K. Lewis, Arlington Heights, both of Ill.

[73] Assignee: Siemens Gammasonics, Inc., Skokie, Ill.

[21] Appl. No.: 852,418

[22] Filed: Nov. 17, 1977

[51] Int. Cl.³ .............................................. A61B 6/00
[52] U.S. Cl. .................................... 128/654; 128/659; 250/363 S; 250/445 T
[58] Field of Search ................ 128/2 A, 2 V, 2.05 Z; 358/111, 112, 113; 250/363 S, 445 T

[56] References Cited

U.S. PATENT DOCUMENTS

| | | | |
|---|---|---|---|
| 3,624,744 | 11/1971 | Munger | 128/2.05 R |
| 3,777,148 | 12/1973 | Miraldi | 250/505 |
| 3,789,833 | 2/1974 | Bom | 128/2 V |
| 3,869,602 | 3/1975 | Sezaki et al. | 235/151.3 |
| 3,936,646 | 2/1976 | Jonker | 250/509 |
| 3,954,098 | 5/1976 | Dick et al. | 128/2.05 Z |
| 4,001,591 | 1/1977 | Imbar | 250/363 S |
| 4,015,592 | 4/1977 | Bradley-Moore | 128/2 A |
| 4,033,335 | 7/1977 | Nickles | 128/2.05 R |
| 4,101,961 | 7/1978 | Reiber | 358/111 X |

OTHER PUBLICATIONS

Wagner et al., "Nuclear Stethoscope", American Journal of Cardiology, vol. 38, p. 747, 11/23/76.
Sano, et al., "Nuclear Cardiology Module for Anger Cameras", SNM 24th Annual MTG, Instrumentation, Jun. 24, 1977.
Chemical and Engineering News, "Radiochemicals Used to Scan The Heart", Dec. 8, 1975, pp. 21–22.

*Primary Examiner*—Robert W. Michell
*Assistant Examiner*—Jeffrey W. Tayon

[57] ABSTRACT

A system and method for obtaining a nuclear kymogram of regional wall motion of an organ under study such as a human heart includes injecting a radioisotope into the blood stream which accumulates in the cardiac blood pool or myocardium. A scintillation camera having a reduced generally elongated area of data recordation is positioned overlying a selected portion of the heart and positional "events" occurring along the major axis of the area of recordation are swept across a CRT in synchronism with the ECG signal. Successive realtime displays each in synchronism with the ECG signal are accumulated to provide a nuclear kymogram.

30 Claims, 13 Drawing Figures

METHOD AND APPARATUS FOR NUCLEAR KYMOGRAPHY PROVIDING A MOTION VERSUS TIME DISPLAY OF THE OUTER TRANSVERSE DIMENSIONS OF AN ORGAN

CROSS REFERENCE TO RELATED APPLICATIONS

This invention is related to co-pending application Ser. No. 852,419 filed Nov. 17, 1977, entitled Unidimensional Nuclear Medical Imager and assigned to the assignee of the present invention which is hereby incorporated by reference. The invention also relates generally to the study of periodic organ motion and more particularly to the study of periodic cardiovascular system operation and most specifically to the study of myocardial wall motion.

Because the cardiac function is one of periodic motion between contraction (called systole) and relaxation (called diastole) numerous methods of study have been provided by which the quality of cardiac function is studied through observation of its periodic motion. However, the criticality of cardiac function gives rise to a number of difficulties in observing the function. For example, in many instances the heart being evaluated is one which is already subject to a number of difficulties and may, indeed, be functioning in a very weak or abnormal condition. Under such circumstances, an evaluation technique which imposes additional stresses upon the cardiac function subjects the patient to substantial risk of further damage or even mortality. Simply stated, the heart which is most in need of evaluation may also, due to the patient's condition, be the heart which is most susceptible to damage by many methods of cardiac study.

In addition, even the most "healthy" cardiac system may be unexpectedly damaged by subjection to severe stress. Also, many forms of cardiac evaluation may involve the administration of substantial doses of high level energy such as X-ray or ultrasound. Quite apart from their effect upon the cardiovascular system, these high energy doses may also produce damage of surrounding or interposed tissue. Effective cardiac study is often rendered even more difficult by additional problems associated with the position of the heart within the subject's anatomy. For example, the human heart is positioned within the protective cavity of the "rib cage" and is partially obscured as a result. In addition, from some viewing angles, the interposed organs, such as the lungs and diaphragm, make evaluation with some techniques from these angles difficult.

The great need for effective cardiac study has led practitioners in the art to develop a number of systems or methods for cardiac evaluation, each of which attempts to surmount one or more of these problems. While each method is effective to some degree, each also represents a compromise between the quality of data achieved and the degree of stress or potential for injury imposed on the subject by the testing procedure.

Perhaps the most commonly used method of cardiac function observation is that generally referred to as contrast angiography or cardiac catheterization in which a catheter is used to inject an X-ray opaque material into the cardiac blood pool or the coronary artery system. Conventional X-ray observation techniques are then employed to produce a photographic image of the blood pool in the former case or coronary artery system in the latter. This method is generally used because of the quality of image produced, however, it does have an associated morbidity and to a small degree mortality. As can be imagined, the injection of the X-ray opaque material from the catheter under pressure imposes a great stress upon the cardiac function. This stress limits the availability of this procedure to patients having existing cardiac problems. In addition to the hazardous aspects, the catheterization procedure is uncomfortable and the equipment utilized is not portable necessitating moving the patient to the equipment. Also, the X-ray dosage used is high further limiting the frequency of safe patient examination. Finally, it has been determined that many of the X-ray opaque materials used in contrast angiography produce subsequent changes in the patient's physiology. This, of course, is extremely undesirable. The dangers and difficulties associated with cardiac catheterization combine to limit it as a general cardiac diagnostic tool.

Another "X-ray" system of cardiovascular motion study is that known as radarkymography in which a fluoroscope is used in conjunction with video tracking. Again, however, problems of high radiation dosage, lack of machine portability and the limited number of views obtainable with this method make its eventual use as a basic heart evaluation tool unlikely.

Nuclear angiography, which involves the study of heart motion by injection into the blood stream of a radioisotope which is traced by its emission of gamma radiation, may also be used to study cardiac function. Different radioisotopes may be selected some of which remain within the cardiac blood pool while others are assimilated by the myocardium (i.e. the cardiac muscle structure). In either case, a scintillation camera is positioned adjacent the heart at the desired angle and periodically "exposed" to a selected portion of the cardiac cycle. Most commonly, a gated-image corresponding to the end of the diastole interval together with one for the end of the systole interval are sought. Cardiac motion is then determined to some extent by a qualitative comparison of the gated end-diastole and end-systole images. Successive exposures over many cardiac cycles are required because of the low level radiation typical of the safely administered radioisotopes. While the gated image technique of nuclear angiography avoids many of the difficulties associated with cardiac catheterization or radarkymography, the images achieved are often difficult to interpret meaningfully on a regional basis. Further, the interpretation is generally limited to qualitative results and the relative durations of systole and diastole cannot be observed.

A system of cardiac evaluation using ultrasound energy, also called "M" mode, has also been developed in which high frequency sound energy is directed into the patient's anatomy and returing "echoes" are evaluated to produce an image. The ultrasound system is perhaps the most desirable approach in the sense that it is the least invasive of all the known systems. However, a number of problems arise which severely restrict the views available using ultrasound techniques. Most importantly, the position of the heart adjacent the lungs, rib cage and diaphragm restrict ultrasound evaluation to a narrow "window" which excludes many critical areas such as the cardiac apex.

Accordingly, it is a general object of the present invention to provide an improved method of cardiac motion study. It is a more particular object of the present invention to provide a less invasive method of cardiac motion study which facilitates the quantitative real-time evaluation of regional myocardial motion.

BREIF DESCRIPTION OF THE FIGURES

The features of the present invention which are believed to be novel are set forth with particularity in the appended claims. The invention, together with further objects and advantages thereof, may best be understood by reference to the following description taken in connection with the accompanying drawings, in the several figures of which like reference numerals identify like elements, and in which:

SUMMARY OF THE INVENTION

A method of producing a quantitatively evaluatable visual representation of periodic regional organ motion, as for example, a cardiovascular system, comprises the steps of causing energy to radiate from at least a portion of the organ; receiving the radiated energy as positional events along a predetermined imaging axis as a function of time; accumulating a plurality of successive positional events in synchronism with the periodic organ motion; and displaying the accumulated plurality of successive recordations to form a continuous two-dimensional image, one of the dimensions depicting time and the other depicting regional organ motion.

DESCRIPTION OF THE PREFERRED EMBODIMENTS

Figure 1:
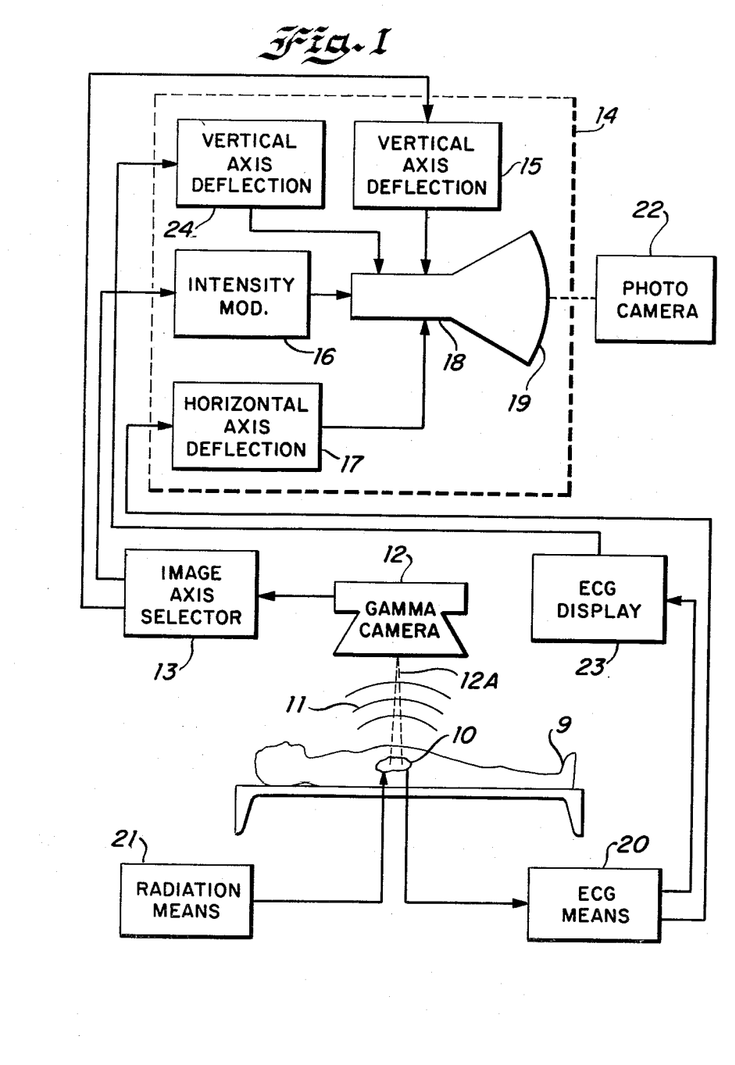
FIG. 1 is a block diagram representation of a system for nuclear kymography constructed in accordance with the present invention.

FIG. 1 shows a block diagram representation of the present invention system of nuclear kymography. An organ of interest 10, in this case a human heart, within a patient anatomy 9 is positioned beneath a gamma camera 12. A radiation means 21 (shown diagrammatically coupled to heart 10) depicts the well-known process in which a radioisotope is injected into the blood stream (not shown) of patient anatomy 9 to cause accumulation of the radioactive substance within either the region, or interior, of heart 10. Radiation means 21 may include, for example, the injection of a radioisotope which collects within the cardiac blood pool as in the case of blood pool kymography, or alternatively a radioisotope which assimilates within the myocardial walls in the case of myocardial kymography.

In either case, however, radiant energy 11 in the form of gamma radiation propagates outwardly from heart 10 toward camera 12. The radiated gamma energy is received by gamma camera 12 and therein converted by means described below in more detail to electrical signals which are coupled to an image axis selector 13. A signal matrix (not shown) within selector 13 processes the output signal of camera 12 producing an electrical signal which includes a recordation of positional events occurring within a restricted field of examination 12a. The second dimensional components within the restricted field are "compressed" in the second dimension direction such that only one dimensional events along the imaging axis are present in the output signal. This one dimensional positional event output signal is applied to a vertical axis deflection system 15 of a CRT 18 within a display system 14. In addition, image axis selector 13 also produces an unblanking signal which is applied to a Z axis intensity modulation system 16 of CRT 18.

Electrocardiogram means (ECG) 20 are responsive to heart 10 and produce a conventional ECG signal which is applied to the synchronization input of a horizontal-axis sweep system 17 of CRT 18 and to an ECG signal display 23. Horizontal-axis sweep 17 includes well-known CRT display circuitry for the generation of a time-varying sweep signal which when applied to the horizontal-deflection axis means of CRT 18 cause the vertical-deflection axis inputs to sweep in time on viewing screen 19. In addition, horizontal-axis sweep 17 includes peak detection circuitry which identifies the "R" wave component of the applied ECG signal and causes the generated sweep signal to be synchronized to the ECG signal. The use of the ECG signal to synchronize horizontal sweep 17 is of particular importance to the present invention because the image thus formed on viewing screen 19 of CRT 18 represents successive cardiac cycles. As successive cardiac cycles and horizontal axis sweeps of viewing screen 19 occur, the vertical-axis deflection and intensity modulation caused by the output signal at image selector 13 produce an image on viewing screen 19 which depicts the spatial distribution of gamma events along the imaging axis (i.e. restricted field of examination 12a) as a function of time. The output of ECG display 23 is coupled to a second vertical-axis deflection 24 and to actuate second vertical deflection 24 and provide simultaneous display of the ECG signal and nuclear kymogram for visual reference.

As in the procedure of nuclear angiography, the level of energy radiation from heart 10 is maintained at a low level to avoid high patient dosage. As a result, the data from a substantial number of cardiac cycles must be accumulated to produce a high quality image. This may be simply accomplished by using a CRT which is of the well-known persistent or storage scope variety. However, a more preferable image is produced if a photo camera 22 having film responsive to the light output of viewing screen 19 is oriented in a proper relationship to viewing screen 19 for exposure of the film to successive CRT images. Further, in situations wherein a digital memory system is available, an even more improved image is provided if data is stored in the digital memory and conventional image processing techniques are applied. In accordance with boundary determination techniques used in other forms of nuclear medicine the one-dimensional output signal of image axis selector 13 may alternatively be processed by numeric techniques to present the accumulated plurality of successive imaging axis events in a numeric format. The use of this alternative facilitates the generation of quantitative data of cardiac function such as total movement, maximum segmental velocity, and average segmental velocity. It will be apparent to those skilled in the art that nuclear kymographic information may be "imaged" in either format that is visual display or numeric "read-out". It will be equally apparent to those skilled in the art that both formats may be concurrently utilized.

Also, at this point, it will be readily apparent to those skilled in the art that the physical orientation between camera 12 and the to-be-studied organ (heart 10) may be varied to select any of a large number of angular projections and bring different aspects of the organ into "view". It will be similarly apparent that the position of restricted examination field 12a of camera 12 with respect to heart 10 may be varied to view selected portions of the organ. In each case the resulting display called a nuclear kymogram provides an image which depicts the cyclical changes of positional events along the selected imaging dimension on a continuous real-time basis. In the case of cardiac evaluation, the resultant image produced clearly shows cyclical regional myocardial wall movement in a quantitatively assessable format.

Figure 2:
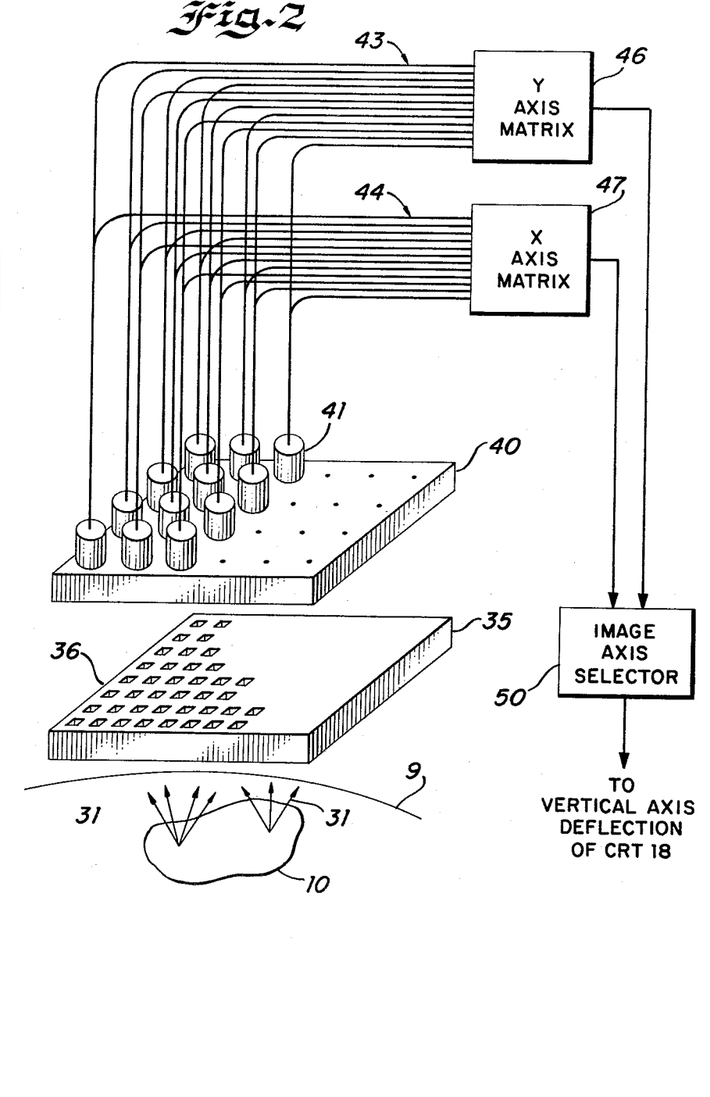
FIG. 2 is a more detailed depiction of gamma camera 12.

Before proceeding to more detailed discussions of the present invention nuclear kymography, a brief description of an Anger-type scintillation camera constructed in accordance with the teachings of U.S. Pat. No. 3,011,057 is believed helpful. FIG. 2 shows a simplified pictorial layout of the major components of a scintillation camera when utilized in accordance with the present invention. The to-be-evaluated organ (heart 10) is shown pictorially radiating gamma energy 11 in the form of a plurality of energy rays 31 propagating in a generally radial pattern from the nuclei of their respective radioisotopes. Because this gamma energy is radiating in a generally incoherent manner, it is in a form virtually useless as an imaging source. The gamma energy is not focusible by conventional optic techniques, therefor a collimator 35 is interposed between the energy emitting organ and the sensing portions of the camera. The fabrication and utilization of such collimators is the subject of considerable variety and refinement within the art; however, all structures utilized may be generally described as being of a gamma absorptive material such as lead in which a plurality of axially directed collimating apertures 36 are defined.

In accordance with basic principles of collimation, the randomly radiating energy 31 is collimated, or converted, to axially directed energy rays which pass through the apertures 36 of collimator 35 to impinge a scintillation crystal 40. Again, as is true of collimators, scintillation crystals are well-known in the art being set forth, for example, in the above-described Anger patent. Scintillation crystals are also subject to some refinement and variation within the art. However, all may be said to perform the basic function of converting the impinging gamma radiation energy to optically perceivable light energy. The principle of scintillation is somewhat complex. However, suffice it to say here that each time a "bundle" of gamma energy strikes scintillation crystal 40 the molecules within the crystal scintillate and a "photo event" occurs which positionally corresponds to the relationship between the original gamma source (i.e. the radioactive nucleus), one of the collimating apertures, and the region of the scintillation crystal stimulated.

A plurality of photomultiplier tubes 41 are positioned in a generally planar array substantially parallel to scintillation crystal 40. Each time gamma energy scintillates a portion of crystal 40 causing a photo event in which light energy radiates from the scintillation crystal area, one or more of the proximately located photomultiplier tubes are energized. The light energy produced is of a distributed nature in which a maximum of light energy is received by the most directly aligned photomultipliers while a minimum is received by those most remotely aligned. The photomultiplier array is connected via a first plurality of connections 43 to a Y axis matrix 46 and via a second plurality of connectors 44 to an X axis matrix 47. In accordance with well-known scintillation camera principles, the positional coordinates of each photo event along the X and Y axes are derived by matrices 46 and 47. As a result, the output of matrices 46 and 47 forms a real-time positional signal of each respective coordinate in the form of electrical impulse signals the amplitudes of which depict the positional relationship along the respective coordinate.

The outputs of matrices 46 and 47 are applied to an image axis selector 50 which may, for example, comprise the well-known "region of interest" feature. Selector 50 provides a restricted area of camera evaluation by selection of X and Y axis information solely within preset limits. In performance of the present invention nuclear kymography, events in the region of interest are converted to events along the imaging by "collapsing" the information to the imaging axis and ignoring the orthogonal component. As a result of this process, the output signal of image axis selector 50 coupled to vertical axis deflection system 15 of CRT 18 provides a succession of electrical pulse signals the polarity and amplitudes of which depict the positional or spatial coordinates of each event along the imaging axis horizontally displayed on a real-time basis.

Figure 3:
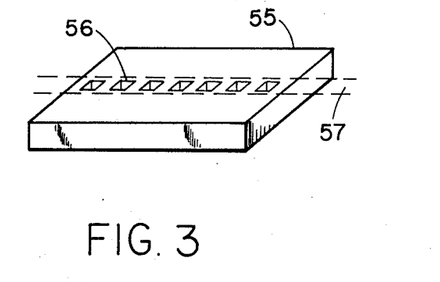
FIG. 3 shows a single axis collimator for use in the present invention system of nuclear kymography.

Not all scintillation cameras are equipped with region of interest imaging, therefore an alternative method for restriction of camera imaging to a selected image axis is provided by a specially designed collimator. FIG. 3 shows a special single-axis collimator 55 in which a plurality of collimating apertures 56 are arranged along a selected imaging axis 57. Collimator 55 is designed to be otherwise interchangeable with collimator 35 and rotatable within camera 12 and when so interchanged restricts scintillation of crystal 40 to gamma events occurring along axis 57. In preferred form, axis 57 is selected to coincide with either of the camera electronic axes (X or Y). In such case the stimualtion of the remaining photomultipliers is minimized which simplifies image axis selection and permits more direct coupling of the selected axis matrix to vertical deflection system 15 of CRT 18. However, often the desired imaging axis will not be a major (X or Y) axis. In such case the full image axis circuitry set forth above is required to perform axis selection data restriction and "collapsing" of the positional component orthogonal to the imaging axis.

As mentioned, special collimator 55 is of particular importance in adapting existing scintillation cameras not having a region of interest capability to performance within the present invention nuclear kymography. However, the need for detection of events occurring along a single imaging axis also makes the use of a single axis scintillation camera, as described in the above-noted co-pending reference application, of particular advantage.

Figure 4:
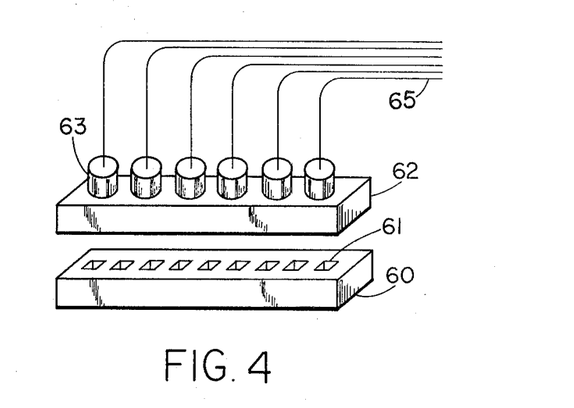
FIG. 4 shows a single axis scintillation camera in accordance with the present invention.

FIG. 4 shows pictorially the basic structure of a single-axis scintillation camera in which an elongated collimator 60 defines a plurality of collimating apertures 61 arranged along a single axis. A similarly elongated scintillation crystal 62 accommodates a corresponding linear array of photomultiplier tubes 63 each of which is connected to display system 14 via a plurality of electrical conductors 65. Because the photomultipliers are arranged in a linear single-axis array, the complex system of matrices used in a two-dimensional scintillation camera is no longer needed. Instead the output signals of photomultiplier tubes 63 are combined in a position matrix the output of which forms a real-time recordation of the positional events along the imaging axis.

Figure 5:
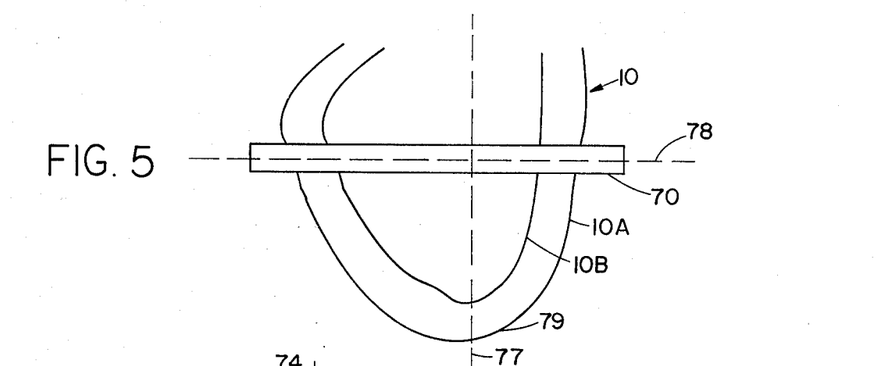
FIG. 5 is a pictorial layout of a cardiac ventricle and overlying imaging area along the minor ventricular axis.

Turning now to the nature of the present invention nuclear kymogram itself, FIG. 5 shows a pictorial representation of the left ventricle of a human heart which defines a long axis 77 terminating in the "apex" 79 and a short axis 78. Outlines 10a and 10b depict the locations of the left ventricle myocardial wall structure during the intervals of end-diastole and end-systole respectively. An imaging dimension, or area, 70 is shown positioned overlying a portion of heart 10 along short axis 78. The area bounded by imaging area 70 approximates the region from which photo events are received and utilized in the present invention nuclear kymography. As mentioned above, nuclear kymography may be pursued using either of two methods. The first, blood pool kymography, results when a radioactive isotope is selected which assimulates within the cardiac blood pool. In this case the change in radiation density at the boundary between the cardiac blood pool and the inner surface of the myocardium are observed. The second, myocardial kymography, results when a radioactive isotope is utilized which is assimulated primarily within the myocardial structure itself. As will be seen, this gives additional information as to muscle "thickening".

Figure 6A:
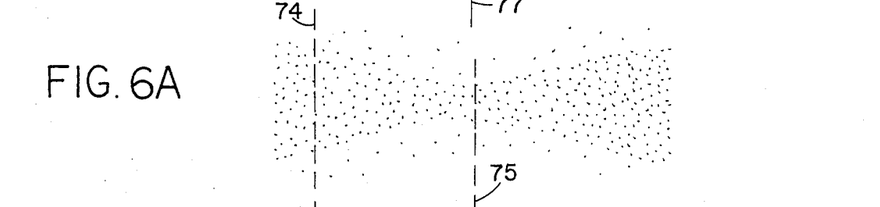
FIGS. 6A thru 6C depicts nuclear kymogram and ECG signals obtained in accordance with the present invention.

FIG. 6A shows a sample nuclear kymogram resulting from blood pool kymography in which the distribution of gamma events along imaging dimension 70 are depicted along the vertical axis while the horizontal axis depicts time. Each "dot" records a gamma event and the high-density region of recorded events (shown in FIG. 6 as a "more shaded" area) defines the outline of the cardiac blood pool. As mentioned, the configuration of the cardiac blood pool within the myocardial structure provides an easily interpreted "view" of the inner boundary of the confining myocardium configuration. The "width" of the blood pool along imaging dimension 70 (i.e. the vertical axis) shows a maximum character during the diastole period 74 indicating that the myocardium has assumed its maximum volume bounded by outline 10a in FIG. 5. Conversely, during the systole period, the blood pool is at a minimum volume bounded by myocardial outline 10b giving the kymogram dimension 75 along imaging axis 70.

Figure 6B:
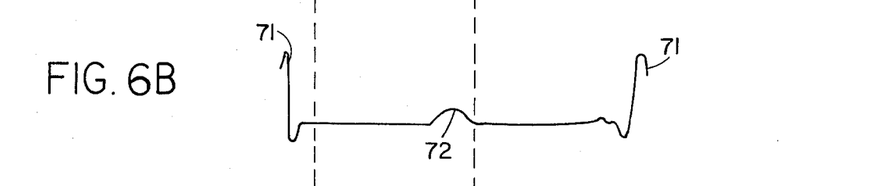

FIG. 6B shows a typical ECG wave form which, as mentioned, is used to synchronize the successive cathode ray tube sweeps to the periodic cardiac cycle. Of particular importance to the present invention system of nuclear kymography are the high amplitude "peak" portions 71 of the ECG signal which are typically referred to as "R waves". These "peak" portions are used to produce a trigger pulse which in turn initiates successive sweeps of CRT 18. In addition, the kymogram obtained by triggering in response to ECG "R" signals is easy to interpret since the generally accepted format of cardiac cycle rests upon common assumption that each cycle is initiated by the ECG R-wave.

Figure 6C:
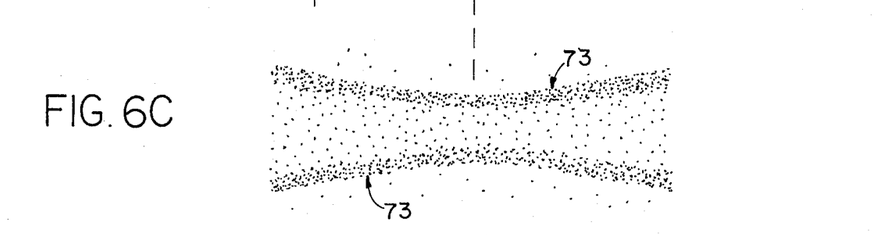

FIG. 6C shows a second nuclear kymogram taken along imaging axis 70 in FIG. 5 in which myocardial rather than blood pool kymography has been pursued. While the general outline of high density shaded area is similar to that shown in FIG. 6A for blood pool kymography, a second gradation 73 may be observed generally along each outer edge of the kymogram high density area. The second gradation defines the myocardium and therefore the dimension of the blood pool derived in FIG. 6A corresponds to the "inner" side of this second gradation. Because this second gradation corresponds to the myocardium itself, the use of myocardial kymography provides additional information not always available in blood pool kymography by recording the changes of myocardium along the imaging axis during the cardiac cycle. Examination of FIG. 6C, for example, shows the characteristic myocardium "thickening" during the systole portion of the cardiac cycle. It should also be noted that the portions of myocardium within imaging axis 70 are each shown (i.e. the top and bottom gradation of FIG. 6C) permitting individual evaluation.

Figure 7A:
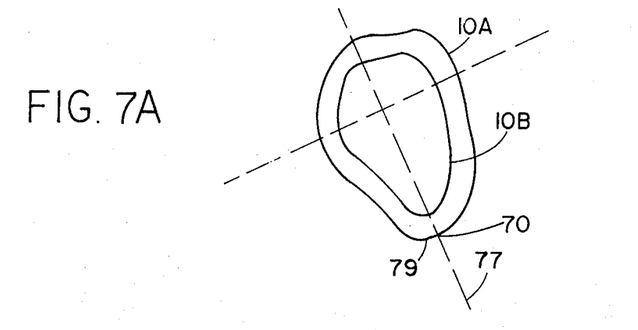
FIG. 7A is a pictorial layout of a cardiac ventricle and overlying imaging area along the major ventricular axis.
Figure 7B:
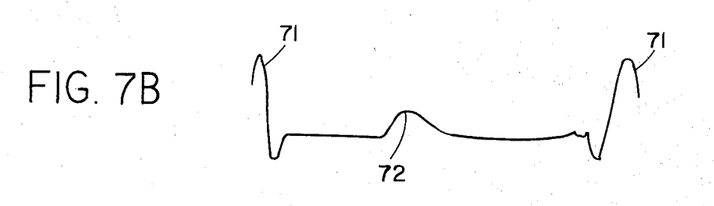
FIGS. 7B thru 7E depict ECG signals and nuclear kymograms of cardiac contraction for systems having differing ejection fractions.
Figure 7C:
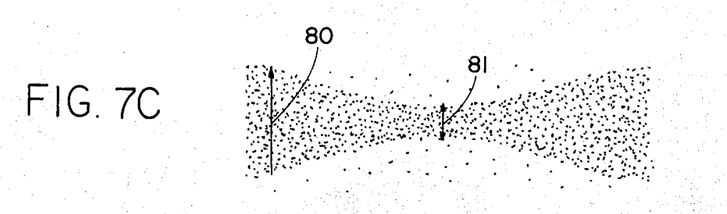
Figure 7D:
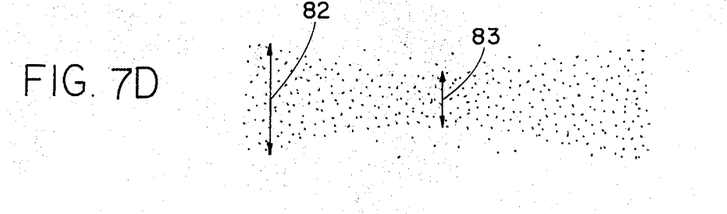
Figure 7E:
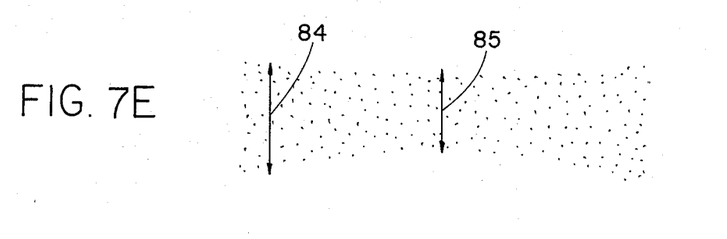

Some indication of the effectiveness of the present invention system of nuclear kymography as a diagnostic tool may be derived by examination of FIGS. 7A through 7E. FIG. 7A again shows a pictorial representation of a human heart left ventricle similar to that of FIG. 5. However, in this instance imaging area 70 now overlies the long axis 77 of heart 10. As in FIG. 5 outline 10a depicts the myocardial boundary location during diastole while outline 10b depicts the myocardial boundary during systole. Also, FIG. 7B shows the ECG wave form similar to that set forth in FIG. 6B defining high intensity R wave peaks 71 and a mid-cycle "T" wave 72 corresponding to ventricular systole. FIGS. 7c, 7d and 7e show long-axis blood pool nuclear kymograms of hearts having ejection fractions of 75%, 50% and 25% respectively. An ejection fraction of 75% is generally considered normal while a 50% ejection fraction is below normal and a 25% ejection fraction characterizes a critical cardiac malfunction. It should be noted at this point that, with appropriate equipment calibration, the nuclear kymograms of FIGS. 7c through 7e may be quantitatively evaluated.

For example, comparison of the respective maximum dimensions 80, 82 and 84 in FIGS. 7c through 7e shows a similar boundary condition or myocardial "breadth" during the diastole period of cardiac function and also each side movement individually. However, a similar comparison of the respective minimum boundary dimensions 81, 83 and 85 shows great variations of the systole performance. Each dimension and the differences between may be measured along the vertical axis facilitating quantitative evaluation. In addition to the quantitative information the kymograms also show a continuous time function display which yields information as to both the relative durations of both systole and diastole periods and the rate of myocardial contraction. The latter is especially useful since it facilitates determination of myocardial compliance. The kymograms also show dramatically the local nautre of myocardium movement. Of great importance, examination of FIG. 7e shows that in addition to the difficulties of extremely small contraction, the myocardium movement produced is "one-sided", that is, only the lower portion, i.e. one wall of the cardiac being examined, is moving.

The present invention method of nuclear kymography described provides improved quantitative regional wall motion study. Because events occurring along the second dimension, (I.E. the dimension orthogonal to the imaging axis) are integrated an improved signal-to-noise ratio is achieved. In addition, because a continuous record of regional wall motion is obtained which is not limited to the time intervals of gating procedures, more accurate quantitative regional wall motion evaluation may be obtained throughout the cardiac cycle and the rate of contraction assessed.

The simultaneous display of the ECG signal with the nuclear kymogram provides a convenient reference for correlation between the cardiac electrical cycle and the cardiac mechanical cycle and a compatible reference for correlating the kymograms to other diagnostic tools. Because the durations of each portion of the cardiac cycle are readily apparent from examination of nuclear kymograms, information in a quantitatively evaluatable form not provided by gated blood pool techniques is achieved. Finally, by appropriate selection of the imaging axis, additional information of myocardial contraction phenomena such as "thickening" of the myocardium and the interventricular septum during systole may be observed and similarly quantitized.

While the above discussions have described the derivation of a single nuclear kymogram, it is desirable in some instances to employ redundant systems for simultaneously producing several nuclear kymograms along different imaging axes. The advantages of simultaneous multiple image axis kymography over sequential may be, for example, reduced patient fatigue, reduced professional time expenditure, and lower patient expense. In addition multiple image axis kymograms which are derived at the same time and radioactive "dose" have an optimum basis for comparison.

It will be apparent to those skilled in the art that while the foregoing descriptions and embodiments have been directed primarily to study of human heart motion, the present invention nuclear kymograms may be used in the study of numerous organs both human and otherwise.

While particular embodiments of the invention have been shown and described, it will be obvious to those skilled in the art that changes and modifications may be made without departing from the invention in its broader aspects, and therefore, the aim in the appended claims is to cover all such changes and modifications as fall within the true spirit and scope of the invention.

We claim:

1. A method of producing a quantitatively evaluatable presentation of periodic regional myocardial wall motion of a cardiovascular system utilizing nuclear analysis, said method comprising the steps of:
   causing nuclear radioactivity to radiate from at least a portion of said cardiovascular system;
   receiving the energy distribution of said radiated energy as positional events along a predetermined imaging axis as a function of time;
   accumulating a plurality of successive positional energy distributions in synchronism with said periodic regional myocardial motion; and
   presenting said accumulated plurality of successive positional energy distributions in the form of a display depicting a unidimensional parameter versus time, said unidimensional parameter defining the outer transverse dimensions and variations in the outer transverse dimensions in the myocardial wall, said display depicting said regional myocardial wall motion as a function of time in order to determine selected parameters of said regional myocardial wall motion.

2. The method set forth in claim 1 wherein said causing step includes the step of injecting a radioisotope into the blood stream in such manner that it circulates to the cardiac blood pool of said cardiovascular system.

3. The method set forth in claim 2 wherein said radioisotope emits gamma radiation and wherein said receiving step includes the steps of:
   positioning a gamma camera adjacent the region of interest of said cardiovascular system; and
   restricting the output of said camera to positional events occurring substantially along said imaging axis.

4. The method set forth in claim 3 wherein said accumulating step includes the step of producing a succession of electrical signals in which the output of said camera is swept in time.

5. The method set forth in claim 4 wherein said accumulating step includes developing an ECG signal of said cardiovascular system and repetitively sequencing said time sweeps of said producing step in synchronism with said ECG signal.

6. The method set forth in claim 5 wherein said presenting step includes:
   applying the sequence of swept signals to one deflection axis of a cathode ray tube;
   repetitively sweeping the other deflection axis in synchronism with said ECG signal; and
   exposing said cathode ray tube image to a photographic camera for a period exceeding a plurality of ECG cycles.

7. The method set forth in claim 5 wherein said presenting step includes the step of adding a display of said ECG signal to provide comparison between said myocardial wall motion and said ECG signal.

8. For use in the evaluation of periodic cardiovascular motion, nuclear analysis kymogram means for producing a display of regional myocardial motion as a function of time, said nuclear analysis kymogram means comprising:
   radiation means causing nuclear energy radiation from at least a portion of said cardiovascular system;
   sensing means receiving the energy distribution of said radiation as positional events along a predetermined imaging axis as a function of time; and
   display means forming a continuous unidimensional parameter versus time display, said unidimensional parameter depicting the outer transverse boundaries of the myocardial wall, said display means comprising means for accumulating a plurality of successive positional energy distributions and displaying said distributions in synchronism with said periodic cardiovascular motion.

9. Kymogram means as set forth in claim 8 wherein said radiation means include a radioisotope introduced into said cardiovascular system in such manner as to accumulate within the cardiac blood pool of said cardiovascular system.

10. Kymogram means as set forth in claim 9 wherein said radioisotope emits gamma radiation and wherein said sensing means include:
   gamma camera means positioned adjacent the region of interest of said cardiovascular system; and
   means restricting the output of said gamma camera means to positional events occurring substantially along said imaging axis.

11. Kymogram means as set forth in claim 10 wherein said accumulating means include a source of ECG signal of said cardiovascular system and wherein said display means further include:

a cathode ray tube having first and second substantially orthogonal deflection axes and an image forming screen;

means coupling the restricted output of said gamma camera means to said first deflection axis;

means causing repetitive sweep of said second deflection axis in synchronism with said ECG signal; and means modulating the intensity of the cathode ray tube image as a function of said positional events.

12. The method set forth in claim 1 wherein said causing step includes the step of injecting a radioisotope into the blood stream in such manner that it circulates to the myocardium of said cardiovascular system.

13. The method set forth in claim 12 wherein said radioisotope emits gamma radiation and whereing said receiving step includes the steps of:

positioning a gamma camera adjacent the region of interest of said cardiovascular system; and restricting the output of said camera to positional events occurring substantially along said imaging axis.

14. The method set forth in claim 13 wherein said accumulating step includes the step of producing a succession of electrical signals in which the output of said camera is swept in time.

15. The method set forth in claim 14 wherein said accumulating step further includes the steps of developing an ECG signal of said cardiovascular system and repetitively sequencing said time sweeps of said producing step in synchronism with said ECG signal.

16. The method set forth in claim 15 wherein said presenting step includes:

applying the sequence of swept signals to one deflection axis of a cathode ray tube;

repetitively sweeping the other deflection axis in synchronism with said ECG signal; and exposing said cathode ray tube image to a photographic camera for a period exceeding a plurality of ECG cycles.

17. The method set forth in claim 15 wherein said presenting step includes the step of adding a display of said ECG signal to provide comparison between said myocardial wall motion and said ECG signal.

18. Kymogram means as set forth in claim 11 wherein said display means include photographic means producing a photographic replica of said cathode ray tube image.

19. Kymogram means as set forth in claim 11 wherein said display means include means simultaneously producing an image depicting said ECG signal.

20. Kymogram means as set forth in claim 8 wherein said radiation means include a radioisotope introduced into said cardiovascular system in such manner as to accumulate within the myocardium of said cardiovascular system.

21. Kymogram means as set forth in claim 20 wherein said radioisotope emits gamma radiation and wherein said sensing means include:

gamma camera means positioned adjacent the region of interest of said cardiovascular system; and means restricting the output of said gamma camera means to positional events occurring substantially along said imaging axis.

22. Kymogram means as set forth in claim 21 wherein said accumulating means include a source of ECG signal of said cardiovascular system and wherein said display means include:

a cathode ray tube having first and second substantially orthogonal deflection axes and an image forming screen;

means coupling the restricted output of said gamma camera means to said first deflection axis;

means causing repetitive sweep of said second deflection axis in synchronism with said ECG signal; and means modulating the intensity of the cathode ray tube image as a function of said positional events.

23. Kymogram means as set forth in claim 22 wherein said display means include photographic means producing a photographic replica of said cathode ray tube image.

24. Kymogram means as set forth in claim 22 wherein said display means include means simultaneously producing an image depicting said ECG signal.

25. Kymogram means as set forth in claim 8 wherein said radiation means emit gamma radiation and wherein said sensing means include a single-axis gamma camera having a substantially elongated energy reception pattern, the major axis of said elongated reception pattern defining said predetermined imaging axis, said single axis gamma camera producing an output signal representative of positional events along said major axis.

26. Kymogram means as set forth in claim 25 wherein said radiation means include a radioisotope introduced into said cardiovascular system, said radioisotope accumulating within a region including said imaging axis in such manner that said myocardial structure is defined by the energy distribution of said gamma radiation along said imaging axis.

27. Kymogram means as set forth in claim 26 wherein said display means include:

a cathode ray tube having first and second deflection axes, said first deflection axis being responsive to said single axis gamma camera output signal;

means deriving an ECG signal for said cardiovascular system;

means causing the second deflection axis to be periodically swept in synchronism with said ECG signal; and means intensity modulating said cathode ray tube upon occurrence of said positional events.

28. A method of producing a quantitatively evaluatable visual representation of periodic regional motion of an organ by nuclear analysis, said method comprising the steps of:

causing nuclear radioactivity to radiate from at least a portion of an internal human or animal organ which normally undergoes periodic motion;

receiving the energy distribution of said radiated energy as positional events along a single predetermined imaging axis as a function of time representing a predetermined organ motion along said imaging axis in terms of dimensions of the organ;

accumulating a plurality of successive positional energy distributions in synchronism with said periodic organ motion; and displaying said accumulated plurality of successive recordations to form a continuous unidimensional motion versus time display, said display defining the outer transverse dimensions of the organ or thickness of the organ wall along said imaging axis, wherein said regional organ motion display depicts the relative dimensions of portions of the organ along said imaging axis, said unidimensional motion versus time display representing the functioning of the organ and providing a unidimensional representation of predetermined selected dimensional organ parameters along said imaging axis.

29. The method set forth in claim 28 wherein said causing step includes the step of injecting a radioisotope into the blood stream in such manner that it circulates to said organ.

30. The method set forth in claim 29 wherein said radioisotope emits gamma radiation and wherein said receiving step includes the steps of:
positioning a gamma camera adjacent the region of interest of said organ; and
restricting the output of said camera to positional events occurring substantially along said imaging axis.

* * * * *